United States Patent
Arcot-Krishnamurthy et al.

(10) Patent No.: US 9,504,819 B2
(45) Date of Patent: Nov. 29, 2016

(54) CARDIAC LEAD PLACEMENT USING MULTIPLE SPATIALLY DISTRIBUTED SENSORS

(71) Applicant: Cardiac Pacemakers, Inc., St. Paul, MN (US)

(72) Inventors: Shantha Arcot-Krishnamurthy, Sammamish, WA (US); Quan Ni, Shoreview, MN (US); Michael J. Stucky, St. Paul, MN (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/842,829

(22) Filed: Sep. 1, 2015

(65) Prior Publication Data

US 2016/0184578 A1  Jun. 30, 2016

Related U.S. Application Data

(62) Division of application No. 12/236,838, filed on Sep. 24, 2008, now Pat. No. 9,149,631.

(60) Provisional application No. 61/007,595, filed on Dec. 13, 2007.

(51) Int. Cl.
*A61N 1/05* (2006.01)
*A61N 1/365* (2006.01)

(52) U.S. Cl.
CPC ........... *A61N 1/056* (2013.01); *A61N 1/36514* (2013.01)

(58) Field of Classification Search
USPC .......... 600/424, 437–438, 509; 607/8–9, 119
See application file for complete search history.

(56) References Cited

U.S. PATENT DOCUMENTS

| 5,891,045 A  | 4/1999 | Albrecht et al. |
| 6,216,027 B1 | 4/2001 | Willis et al. |
| 6,246,898 B1 | 6/2001 | Vesely et al. |
| 6,628,988 B2 | 9/2003 | Kramer et al. |
| 6,795,732 B2 | 9/2004 | Stadler et al. |
| 6,915,149 B2 | 7/2005 | Ben-Haim |

(Continued)

OTHER PUBLICATIONS

Heist, Kevin E. et al., "Radiographic Left Ventricular-Right Ventricular Interlead Distance Predicts the Acute Hemodynamic Response to Cardiac Resynchronization Therapy", The American Journal of Cardiology, 2005, 6 pages.

(Continued)

*Primary Examiner* — Paula J Stice
(74) *Attorney, Agent, or Firm* — Faegre Baker Daniels LLP

(57) ABSTRACT

A system for facilitating placement of a lead in or on a patient's heart includes a first lead apparatus, a second lead apparatus, a user interface, and a processor. The processor is configured to measure a distance parameter indicative of a distance between a reference sensor element at a right heart location and a lead apparatus sensor element at each of a plurality of left heart locations in either the left ventricle or a coronary venous pathway, determine a separation distance for each of the plurality of left heart locations from the right heart location based on the distance parameter measurements, and determine that the separation distance for a location of the plurality of left heart locations from the right heart location is less than a threshold distance based on the separation distance for the location. The threshold distance representative of unsuitability for pacing.

9 Claims, 8 Drawing Sheets

(56) References Cited

U.S. PATENT DOCUMENTS

| | | |
|---|---|---|
| 7,200,439 B2 | 4/2007 | Zdeblick et al. |
| 7,203,541 B2 | 4/2007 | Sowelam et al. |
| 7,233,821 B2 | 6/2007 | Hettrick et al. |
| 9,149,631 B2 | 10/2015 | Arcot-Krishnamurthy et al. |
| 2002/0087089 A1 | 7/2002 | Ben-Haim |
| 2004/0098056 A1 | 5/2004 | Ding et al. |
| 2005/0027323 A1 | 2/2005 | Mulligan et al. |
| 2005/0203579 A1 | 9/2005 | Sowelam et al. |
| 2005/0288727 A1 | 12/2005 | Penner |
| 2007/0055151 A1 | 3/2007 | Shertukde et al. |
| 2009/0157090 A1 | 6/2009 | Arcot-Krishnamurthy et al. |

OTHER PUBLICATIONS

International Preliminary Report on Patentability issued in PCT/US2008/086520, issued Jun. 15, 2010, 8 pages.

International Search Report and Written Opinion issued in PCT/US2008/086520, mailed Apr. 2, 2009, 11 pages.

Shuros, Allan C., et al. Ventricular Preexcitation Modulates Strain and Attenuates Cardiac Remodeling in a Swine Model of Myocardial Infarction. Circulation, 116:1162-1169, 2007.

|  | Infarct | Border | Viable |
|---|---|---|---|
| Electrical | - | + | + |
| Mechanical | - | - | + |
| + → indicates no change due to infarction ||||
| - → indicates change due to infarction ||||

| Distance measure | | |
|---|---|---|
| Anchor Crystal | Last Position (#1) (mm) | Current Position (#2) (mm) |
| RV | 25 | 40 |
| RA | 80 | 70 |
| Other | ... | ... |

| Mechanical timing measure | | |
|---|---|---|
| Mechanical Measure | Last Position (#1) (ms) | Current Position (#2) (ms) |
| Local Max Strain | ... | ... |
| Time to Peak Displacement | ... | ... |
| Other Mechanical Timings | | |

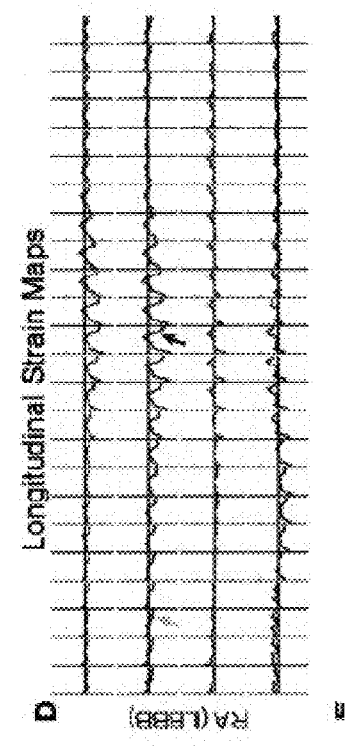
Figure 9A
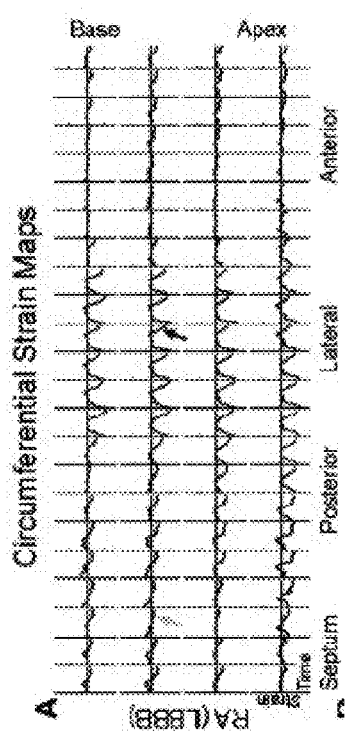
Figure 9B
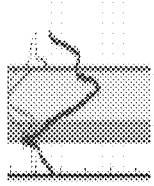
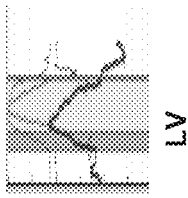
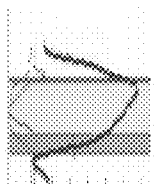
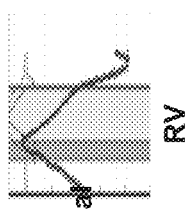
Figure 10A
Figure 10B

CARDIAC LEAD PLACEMENT USING MULTIPLE SPATIALLY DISTRIBUTED SENSORS

CROSS-REFERENCE TO RELATED APPLICATION

This application is a division of U.S. application Ser. No. 12/236,838, filed Sep. 24, 2008, which claims priority to Provisional Application No. 61/007,595, filed Dec. 13, 2007, all of which are herein incorporated by reference in their entirety.

TECHNICAL FIELD

The present invention relates generally to cardiac lead delivery and, more specifically, to cardiac lead placement using a multiplicity of spatially distributed sensors.

BACKGROUND

When functioning normally, the heart produces rhythmic contractions and is capable of pumping blood throughout the body. The heart has specialized conduction pathways in both the atria and the ventricles that enable the rapid conduction of excitation impulses (i.e. depolarizations) from the SA node throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart are coupled to electrodes that sense the heart's electrical signals and for delivering stimulation to the heart in accordance with various therapies for treating cardiac arrhythmias.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

Pacing therapy has been used in the treatment of heart failure (HF). HF causes diminished pumping power of the heart, resulting in the inability to deliver enough blood to meet the demands of peripheral tissues. HF may cause weakness, loss of breath, and build up of fluids in the lungs and other body tissues. HF may affect the left heart, right heart or both sides of the heart. For example, HF may occur when deterioration of the muscles of the heart produce an enlargement of the heart and/or reduced contractility. The reduced contractility decreases the cardiac output of blood and may result in an increased heart rate. In some cases, HF is caused by unsynchronized contractions of the left and right heart chambers, denoted atrial or ventricular dysynchrony. Particularly when the left or right ventricles are affected, the unsynchronized contractions can significantly decrease the pumping efficiency of the heart.

Pacing therapy to promote synchronization of heart chamber contractions to improve cardiac function is generally referred to as cardiac resynchronization therapy (CRT). Some cardiac pacemakers are capable of delivering CRT by pacing multiple heart chambers. Pacing pulses are delivered to the heart chambers in a sequence that causes the heart chambers to contract in synchrony, increasing the pumping power of the heart and delivering more blood to the peripheral tissues of the body. In the case of dysynchrony of right and left ventricular contractions, a biventricular pacing therapy may pace one or both ventricles. Bi-atrial pacing or pacing of all four heart chambers may alternatively be used.

SUMMARY

Example 1 is a system for facilitating placement of a lead in or on a patient's heart includes a first lead apparatus, a second lead apparatus, a user interface, and a processor. The first lead apparatus is configured for positioning a reference sensor element at a right heart location, the right heart location in either the right atrium or right ventricle. The second lead apparatus is configured to advance a cardiac electrode to a left heart site of the patient's heart. The second lead apparatus includes at least one lead apparatus sensor element. The processor is coupled to the user interface, the reference sensor element, and the lead apparatus sensor element. The processor is configured to measure, using signals produced by the reference and lead apparatus sensor elements, a distance parameter indicative of a distance between the reference sensor element at the right heart location and the at least one lead apparatus sensor element at each of a plurality of left heart locations in either the left ventricle or a coronary venous pathway, determine a separation distance for each of the plurality of left heart locations from the right heart location based on the distance parameter measurements, and determine that the separation distance for a location of the plurality of left heart locations from the right heart location is less than a threshold distance based on the separation distance for the location. The threshold distance representative of unsuitability for pacing, the processor configured to cause the interface to produce a physician perceivable output indicating the unsuitability for pacing at the location.

In Example 2, the system of Example 1, wherein the first and second lead apparatuses respectfully comprise a cardiac electrical lead having one or more electrodes configured for electrical stimulation of cardiac tissue.

In Example 3, the system of Example 1, wherein the first lead apparatus comprises a catheter, and the second lead apparatus comprises a cardiac electrical lead having one or more electrodes configured for electrical stimulation of cardiac tissue.

In Example 4, the system of any of Examples 1-3, wherein the reference sensor element and the apparatus sensor element respectively comprise an ultrasonic sensor.

In Example 5, the system of any of Examples 1-3, wherein the reference sensor element and the apparatus sensor element respectively comprise a piezoelectric sensor, a piezoresistive sensor, a strain sensor, an accelerometer, an optical displacement sensor, or a deformation sensor.

In Example 6, the system of any of Examples 1-5, wherein the user interface comprises a display, and the processor is configured to display an alert or warning indicating that the separation distance for the location of the plurality of left heart locations from the right heart location is less than the threshold distance for physician viewing on the display during lead placement.

In Example 7, the system of any of Examples 1-6, further including a third lead apparatus configured for positioning a second reference sensor element at a right heart location, wherein the right heart location is in right atrium if the first lead apparatus is in the right ventricle, or the right heart location is in the right ventricle if the first lead apparatus is in the right atrium, wherein the processor is further coupled to the second reference sensor element, the processor configured to determine a location of the second lead apparatus using signals produced by the reference sensor element, the second reference sensor element, and the at least one lead apparatus sensor element.

In Example 8, the system of claim 7, wherein the third lead apparatus further includes a third reference sensor element and the processor is further coupled to the third reference sensor element, wherein the processor is configured determine the location of the second lead apparatus using signals produced by the reference sensor element, the second reference sensor element, the third reference sensor element, and at least one lead apparatus sensor element.

In Example 9, the system of claim 8, wherein the processor is configured to determine the location of the second lead apparatus by computing a time difference of arrival of a signal emitted from the at least one lead apparatus sensor element to each of the reference sensor element, the second reference sensor element, and the third reference sensor element.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 9A-10B show strain maps or portions thereof that may be developed in accordance with embodiments of the present invention and presented to the physician to aid in lead placement;

Figure 1:
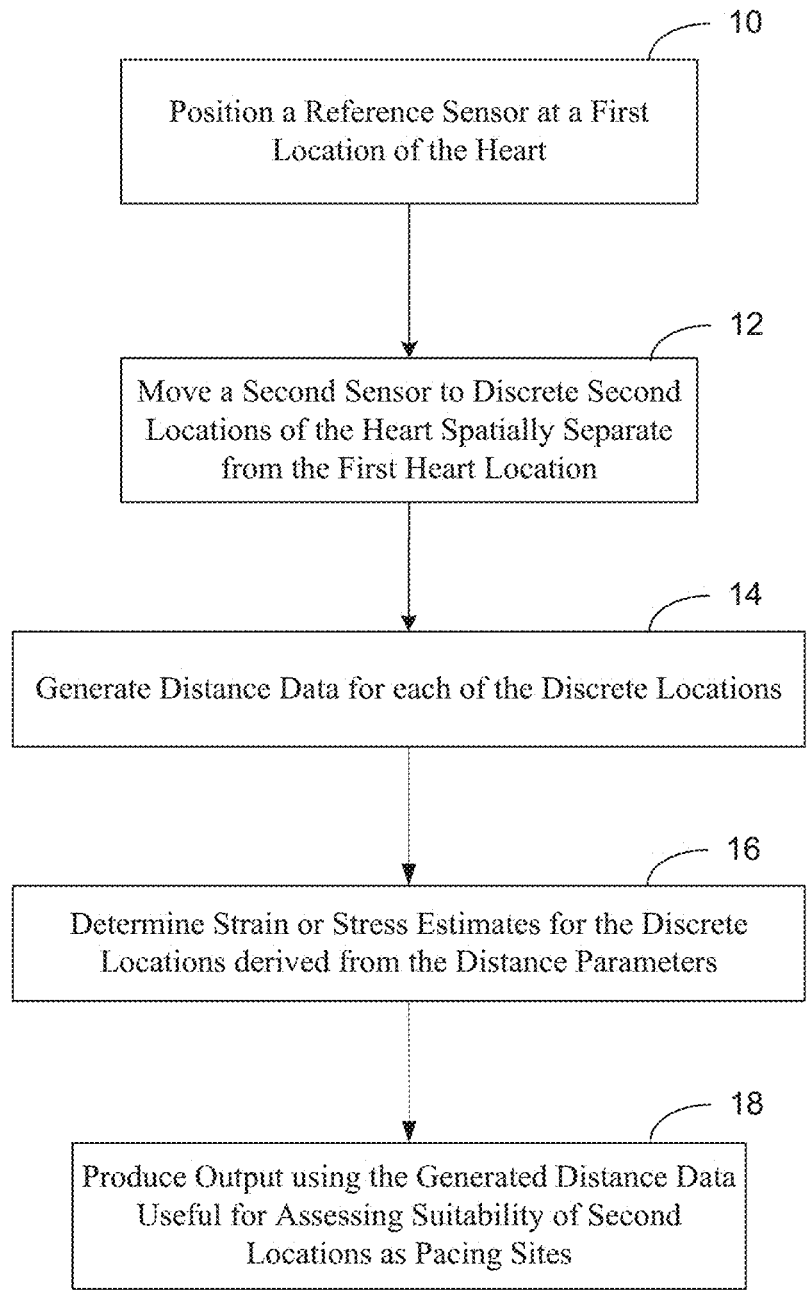
FIG. 1 is a flow diagram showing various processes of a cardiac lead placement method in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device, system or methodology may be implemented to provide a variety of therapeutic or diagnostic functions.

Embodiments of the invention are directed to systems and methods for assisting physicians during lead placement and electrode implantation. Aspects of the invention are directed to evaluating cardiac tissue, such as candidate pacing sites, using multiple sensors situated on one or more leads, on one or more lead placement apparatuses, or on both a lead and a lead placement apparatus. Various embodiments of the invention employ a multiplicity of spatially distributed sensors configured to sense cardiac mechanical motion.

Suitable sensors include ultrasonic sensors, piezoelectric sensors, piezoresistive sensors, strain sensors, accelerometers, and optical displacement or deformation sensors, among others. Various measurements are made using the multiplicity of spatially distributed sensors, such as distance between sensors measurements, measurements derived from distance data, local and/or global strain measurements, mechanical delay measurements, and electro-mechanical delay measurements. In the case of ultrasonic sensors, distance measurements and/or strain measurements derived from distance measurements are preferably made using a sonometric measuring technique. Suitable sonometric distance measuring techniques and distance sensing arrangements are disclosed in U.S. Pat. Nos. 7,233,821 and 6,795,732, which are incorporated herein by reference. Results of distance measurements and/or strain or stress measurements derived from distance measurements are preferably presented to a physician for purposes of guiding lead placement, such as by indicating suitability of cardiac tissue locations as potential pacing sites. These results may be presented in various forms, such as one or more of data, text, indicia, graphics, imaging or other forms.

According to various embodiments, methods are directed to guiding cardiac lead placement using displacement sensors situated on the cardiac lead and/or the lead placement apparatus. Displacement information developed from the displacement sensors may be used to estimate distance of one sensor relative to another sensor, from which an estimate of anatomical location of the cardiac lead may be made as the lead is advanced by the physician. The displacement information may be used to derive other distance-based parameters, such as strain or velocity. Mechanical information derived from the displacement sensors may be used to determine mechanical delay characteristics of cardiac tissue, which may be combined with electrical activity information to provide electro-mechanical delay information for physician use. With the electrical delay information and mechanical delay information derived from analysis of distance data, a lead/pacing pole may be guided to the region with larger mechanical and/or electromechanical delay.

According to various embodiments, one or more distance sensors may be situated close to the distal tips of one or more leads and/or lead placement apparatuses. One or more distance sensors may be distributed along the lead body or along a sheath of a lead placement apparatus. Distance and/or a derivative parameter of distance between the lead(s) and/or lead placement apparatus(es), and thus candidate pacing sites, may be continuously monitored. Candidate pacing sites may be evaluated on the basis of one or more of separation distance (e.g., maximum separation distance), stress or strain (e.g., regions of maximum or uniform strain or stress), mechanical delay, electrical delay, and electromechanical delay.

Based on patient needs, the distance-based information may be used by the physician to select a suitable pacing site and to guide a cardiac lead/electrode to the selected pacing site. An imaging tool, such as echocardiography, may also be implemented into the system to provide automated feedback regarding the performance of the heart, optimizing pacing site selection, and pacing parameters. Influence of breathing may also be removed by a pre-set filter or by averaging a certain n number of beats. Reducing, minimizing or eliminating the influence of breathing is often necessary as the distance and strain/stress measure might change depending on which phase of the respiratory cycle it was measured from.

Turning now to the figures, FIG. 1 is a flow diagram showing various processes of a cardiac lead placement method in accordance with embodiments of the present invention. According to the embodiment shown in FIG. 1, a reference sensor is positioned 10 at a first location of a patient's heart. A second sensor is moved 12 along the heart at locations spatially separate from the first reference sensor. Preferably, the second sensor is moved to a multiplicity of discrete second locations of the heart for purposes of making one or more measurements, it being understood that such measurements may be made while the second sensor is continuously moved. Distance data is generated 14 for each of the discrete second locations of the heart. The distance data may include a measurement of separation distance between the first and second sensors and/or a measurement that can be derived from separation distance information.

Strain or stress estimates are determined 16 for the discrete second locations of the heart derived from the distance parameters. According to embodiments, an output is generated 18 indicative of one or more of the distance data measurements, strain estimates, and stress estimates. The output is preferably of a type that is useful to the physician for assessing structural, mechanical, electrical, and/or electrical-mechanical characteristics of the patient's heart. For example, the output is preferably of a type that is useful to the physician for assessing suitability of the multiplicity of second locations as pacing sites.

According to various embodiments, one or more sensors may be situated on a right ventricular lead, lead delivery apparatus or catheter and positioned at the apical region. One or more sensors may be situated on a left ventricular lead, lead delivery apparatus or catheter and moved along the left ventricle (or vice-versa). A right atrial lead, lead delivery apparatus or catheter may support one or more sensors and be positioned in the right atrium to serve as a reference for atrial-to-ventricle electrical or mechanical delay measurements. The can or housing of an implantable medical device, such as a cardiac rhythm management system or implantable cardioverter/defibrillator, may itself be used as a reference by inclusion of an appropriate sensor.

Embodiments of the present are directed to an acute methodology of making distance measurements using a multiplicity of implantable sensors, in which at least one of the sensors is removed from the patient's body upon completion of the medical procedure (e.g., lead delivery/placement procedure). Acute methodologies of the present invention are directed to enhancing physician evaluation of candidate pacing sites during a lead placement procedure. According to such embodiments, one or more sensors are typically disposed on a catheter (e.g., sensor catheter or lead delivery catheter) and positioned at a location within the right atrium or right ventricle, for example. Once positioned, the right heart sensor(s) may be used as a positional reference, by virtue of being situated at a relatively fixed position within the heart.

A lead or lead delivery catheter may be provided with one or more sensors. The lead/lead delivery catheter may be configured for left heart access, such as epicardial access or transvenous (via the coronary sinus and coronary venous pathway, for example). The lead/lead delivery catheter is advanced along the left heart tissue and various distance-based measurements are taken, preferably at discrete left heart locations, using sensor data produced by the spatially distributed sensors at right and left heart positions. Distance-based measurement data is preferably communicated to the physician performing the lead placement procedure. As discussed above, the distance-based measurement data is preferably of a type that is useful to the physician for assessing structural, mechanical, electrical, and/or electrical-mechanical characteristics of the patient's heart, such as for assessing suitability of discrete left heart locations as pacing sites.

Obtaining distance-based measurements in accordance with the present invention is particularly useful when delivering left heart leads for heart failure patients. It is theorized that a heart failure patient's response to cardiac resynchronization therapy is enhanced when pacing electrodes are widely separated, so that a large volume of ventricular tissue interposes the pacing electrodes. For example, to promote better synchronization between the right and left ventricles, it may be beneficial to place the RV and LV electrodes relatively far apart.

Distance-based measurements obtained in accordance with the present invention provides the physician with lead/electrode separation distances during lead placement, so that the RV and LV electrodes can be implanted with an appropriate separation distance therebetween. For example, a discrete left heart location that provides a maximum separation distance relative to a right heart reference sensor location may be selected as a desired (e.g., optimal) location for implanting an LV electrode. The physiologic basis for spacing the RV and LV electrodes widely, rather than closely, is discussed, for example, in Radiographic Left Ventricular-Right Ventricular Interlead Distance Predicts the Acute Hemodynamic Response to Cardiac Resynchronization Therapy, The American Journal of Cardiology, Volume 96, Issue 5, 1 September 2005, Pages 685-690).

By way of further example, incremental distance-based measurements may be made using left and right heart sensors. The distance-based measurements may be used to derive strain or stress measurements, such as by using distance curves developed using distance measurements. Distance curves may be used to provide an estimate of cardiac tissue stress or strain throughout the cardiac cycle, such as in the manner discussed in Ventricular Preexcitation Modulates Strain and Attenuates Cardiac Remodeling in a Swine Model of Myocardial Infarction, Shuros et al, Circulation. 2007 116.

It is theorized that a heart failure patient's response to cardiac resynchronization therapy is enhanced when pacing electrodes at or near ventricular tissue that is under greater (or greatest) strain or stress relative to other regions of the ventricle. Strain or stress measurements derived from distance measurements obtained in accordance with the present invention provides the physician with a mapping of cardiac tissue stress or strain, so that the LV electrode(s) can be implanted at or near those regions of greater or greatest strain/stress for purposes of unloading these regions. The LV electrode(s) may alternatively, or in addition, be positioned at a region or regions that provide the most uniform stress or strain distribution.

Figure 2:
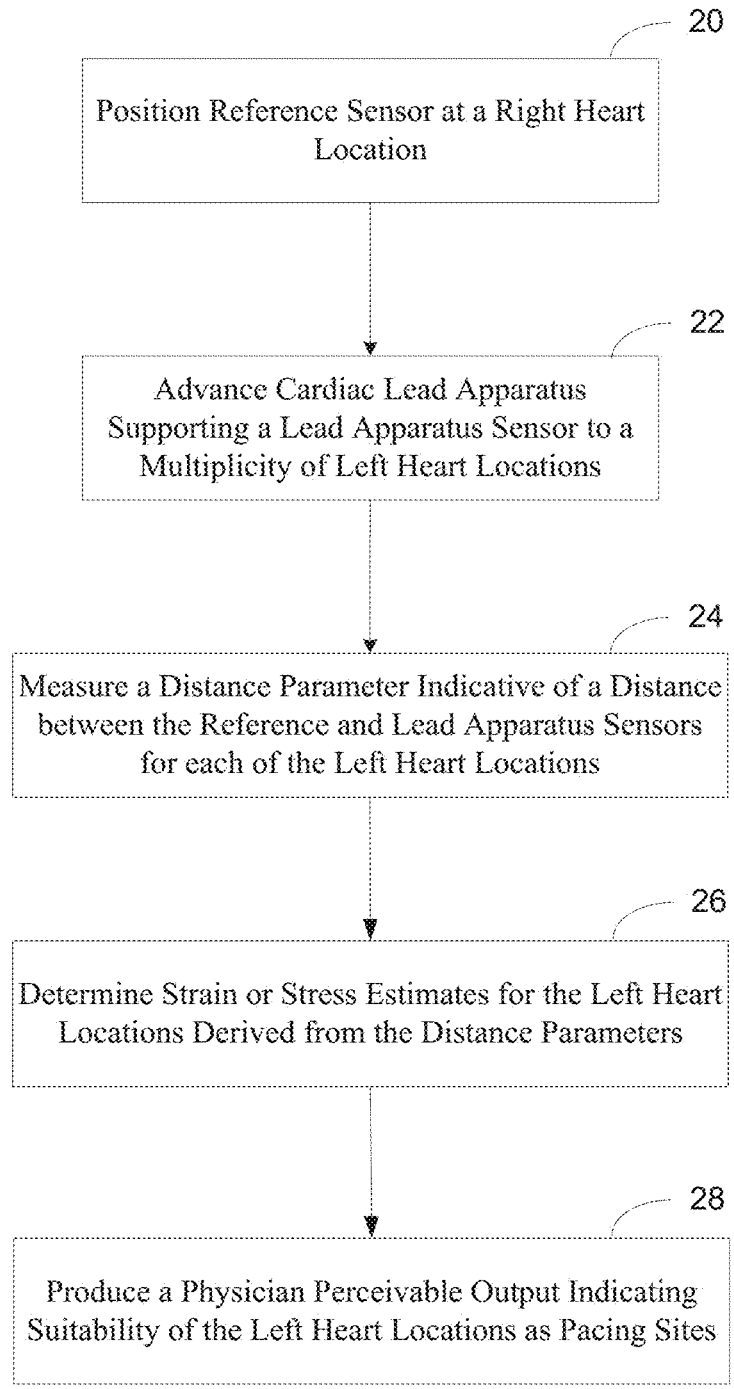
FIG. 2 is a flow diagram showing various processes of a cardiac lead placement method in accordance with embodiments of the present invention.

FIG. 2 is a flow diagram showing various processes of a cardiac lead placement method in accordance with embodiments of the present invention. According to the embodiment shown in FIG. 2, a reference sensor is positioned 20 at a right heart location of a patient's heart. A cardiac lead apparatus is provided that supports at least one lead apparatus sensor. The lead apparatus may be a medical electrical lead, a lead delivery catheter or sheath, or a combined lead/lead delivery apparatus. The lead apparatus is advanced 22 to a multiplicity of left heart locations. A distance parameter is measured 24 for each of the left heart locations, the distance parameter indicative of a distance between the reference sensor and the lead apparatus sensor.

Strain or stress estimates are preferably determined 26 for the left heart locations derived from the distance parameters. A physician perceivable output developed from one or more of the measured distance parameters, strain estimates, and stress estimates is produced 28. For example, the physician perceivable output may indicate the suitability of the left heart locations as pacing sites. By way of further example, the physician perceivable output may include an alert or warning indication that the spacing between right and left heart electrodes is too small (e.g., separation distance <1 cm or <2 cm) or that the region is of lower strain/stress relative to other regions, and that this pacing site should not be considered a good candidate pacing site relative to others.

Figure 3:
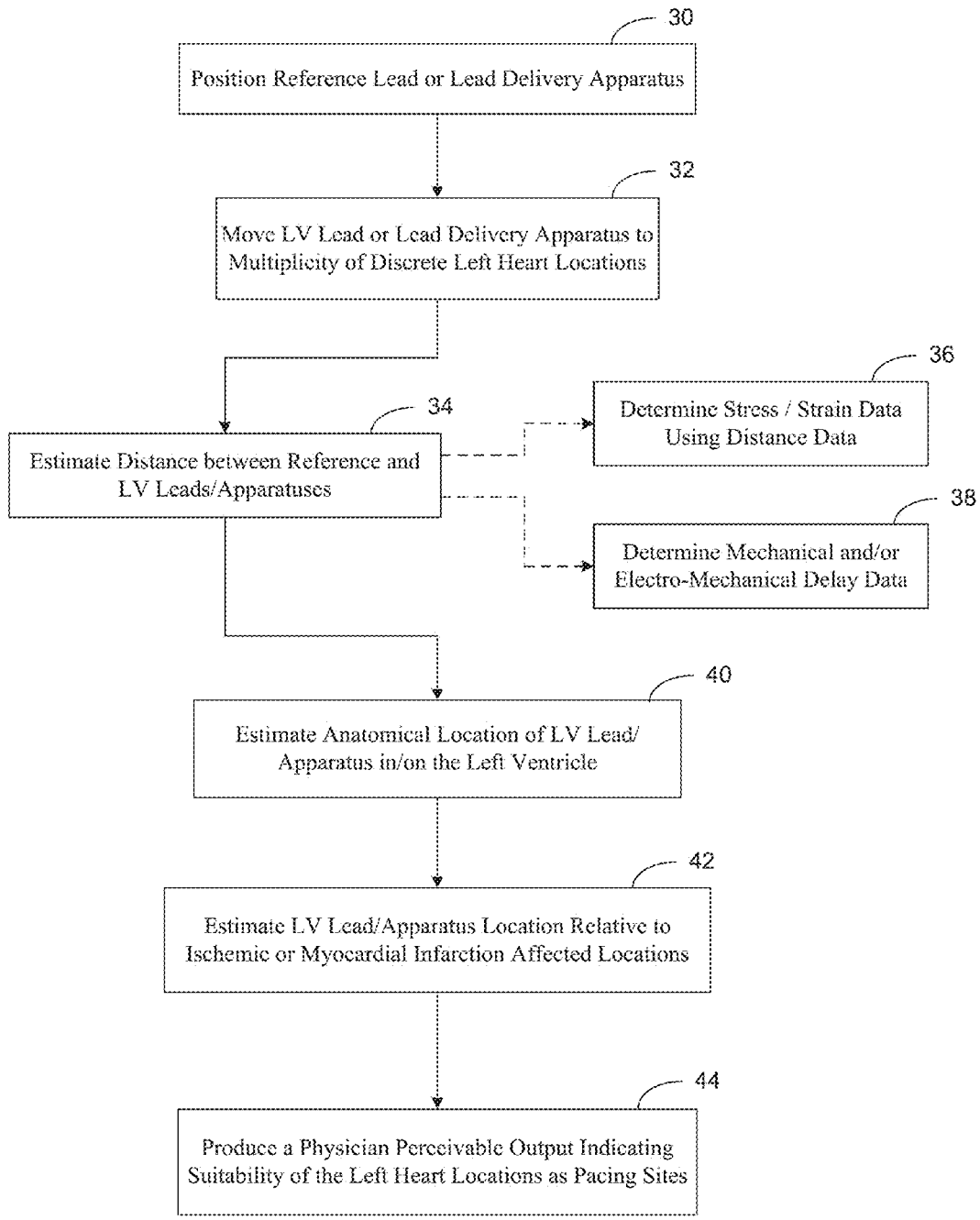
FIG. 3 is a flow diagram showing various processes of a cardiac lead placement method in accordance with embodiments of the present invention.

FIG. 3 is a flow diagram showing various processes of a cardiac lead placement method in accordance with embodiments of the present invention. According to the embodiment shown in FIG. 3, a reference lead or lead delivery apparatus that supports one or more sensors is positioned 30 at a desired location. The desired location may be in the right ventricle or right atrium of a patient's heart. An LV lead or lead delivery apparatus that supports one or more lead apparatus sensors is moved 32 to a multiplicity of discrete left heart locations. A distance parameter is measured 34 to provide an estimate of separation distance between the reference and lead apparatus sensors for each of the left heart locations, thereby providing a measure of separation distance between the lead tips or pacing poles. As is shown in FIG. 3, strain or stress data may be computed 36 based on the distance estimates. Alternatively, or in addition, mechanical and/or electro-mechanical delay data may be determined 38 using the distance estimates and, in the case of electro-mechanical delay data, electrical activity data acquired from the electrode(s) of the leads/lead delivery apparatuses (which may include use of a can or indifferent electrode).

Figures 4, 5:
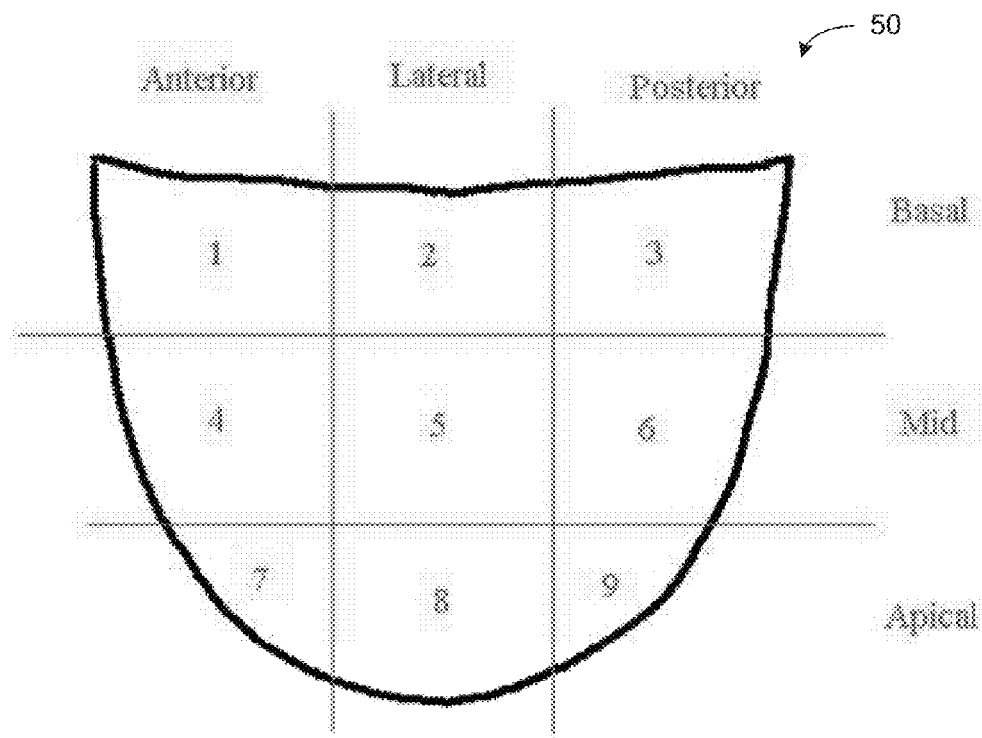
FIG. 4 shows various regions of a patient's heart on a heart map that may be used to facilitate cardiac lead placement in accordance with embodiments of the present invention.
FIG. 5 is a table of electrical and mechanical characteristics that may be used to identify ischemic and myocardial infarction (MI) affected myocardium, viable myocardium, and a border region between ischemic/MI affected and viable myocardium to facilitate cardiac lead placement in accordance with embodiments of the present invention.

It may be desirable to provide the physician with an estimate of the anatomical location 40 of the LV lead or lead delivery apparatus in or on the left ventricle during lead placement. FIG. 4 shows various regions of the heart 50 on a heart map. The left ventricular regions may be classified according to nine regions in the manner shown in FIG. 4. Other ways to classify the ventricular regions of interest are contemplated. Depending on the distance measured between the reference sensor (e.g., RV or RA sensor) and the LV lead/lead delivery apparatus sensor, the position of the LV lead/lead delivery apparatus may be shown on a map of the left ventricle, such as that shown in FIG. 4.

The heart maps may be generated in real-time during the placement and implant procedure. The range of distances may be decided based on similar heart size population. Knowing the approximate location of the reference sensor, separation distance between the reference sensor and the LV lead/lead delivery apparatus sensor, and using a heart map appropriate for the particular patient, the approximate anatomical location of the LV lead/lead delivery apparatus may be determined. The anatomical location information may be communicated to the physician in real-time to facilitate lead placement.

From the continuous measure of distance between the multiplicity of spatially distributed sensors, a guide about where the lead(s) is on the ventricular wall can be determined. A population-based (heart/ventricular-size based) estimate of distances from the RV apical lead tip to the LV regions, for example, can be obtained and used to guide or map the location of the LV lead. The different LV locations may be relatively simple as shown in FIG. 4. Maps for specific RV and/or LV locations and with better resolution can be generated for enhanced guidance. If the anatomical position of where the lead needs to be placed is decided or estimated, then the map may be used to identify if the lead is close to the region of interest.

As a lead is advanced further through the different regions of the heart or just prior to deciding on the optimal lead location, the region may be evaluated 42 to ensure that it is not an ischemic or myocardial infarction (MI) affected region. This evaluation 42 may be performed using known imaging techniques. Alternatively, or in addition, capture voltage levels may evaluated to determine if large voltage changes result from capture testing at a given region. A significant increase in voltage needed to effect capture may signify ischemic/MI affected myocardium.

Another approach to evaluating a region of the heart to determine presence of ischemic/MI affected myocardium involves charting electrical and mechanical characteristics or morphology of the region. FIG. 5 is a table that may be used in such an evaluation. The table shown in FIG. 5 may be used to identify ischemic/MI affected myocardium, viable myocardium, and a border region between ischemic/MI affected and viable myocardium. For example, a region of ventricular tissue may be evaluated using techniques of the present invention, from which electrical and mechanical characteristics may be derived.

As shown in FIG. 5, observable changes in both electrical and mechanical characteristics occur when moving the lead/lead delivery apparatus from viable myocardium to ischemic/MI affected myocardium (a change in sign in FIG. 5 from negative to positive or vice-versa). Moving the lead/lead delivery apparatus from ischemic/MI affected myocardium to bordering tissue generally results in an observable change in electrical, but not mechanical, characteristics. Hence, it may be desirable to obtain both mechanical and electrical measurements in accordance with certain embodiments, when avoiding ischemic/MI affected myocardium during a lead placement procedure is of heightened importance.

It is understood that other methodologies for detecting ischemic/MI affected myocardium may be employed, alternatively or in addition to those discussed above. According to one lead placement approach, for example, prior to final lead implantation, an ischemic/MI affected myocardium location algorithm may be automatically triggered to ensure that the lead is not placed in an ischemic or infarct region.

Figures 6, 7, 8:
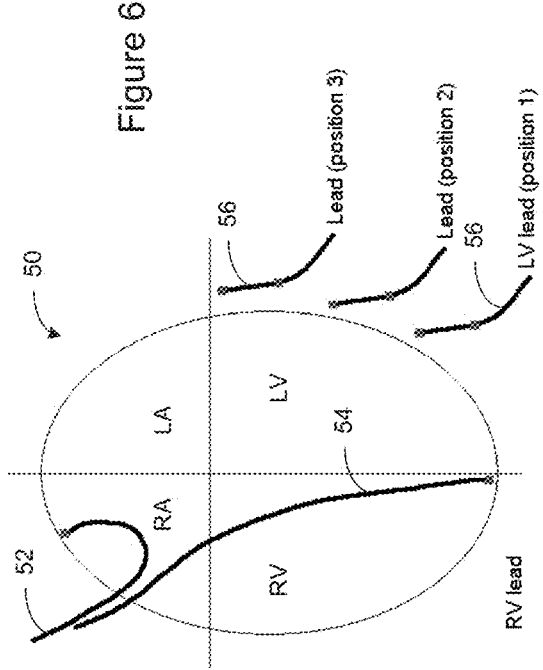
FIG. 6 is an illustration of a patient's heart and a lead placement apparatus implemented in accordance with embodiments of the present invention.
FIGS. 7 and 8 are tables that may be used to store and/or display information that may be useful to the physician during a lead placement procedure in accordance with embodiments of the present invention.

FIG. 6 is an illustration of a patient's heart 50 and a lead placement apparatus implemented in accordance with embodiments of the present invention. FIG. 6 shows a right heart lead apparatus 52 placed within the right atrium. A right heart lead apparatus 54 is shown placed in the right ventricle. A left heart lead apparatus 56 is shown in FIG. 6 as having been moved to three discrete left heart positions (positions 1, 2, and 3, ranging between apical, mid, and basal locations of the left ventricle). The term lead apparatus is intended to refer to various types of apparatuses, including, but not limited to, leads, lead delivery apparatuses, catheters, sheaths, and probes, for example.

As was previously discussed, the right heart lead apparatus is preferably situated at a right heart location so that its sensor(s) may be used as a relatively fixed reference. In general, a single right heart lead apparatus (ventricular or atrial) is employed, notwithstanding that FIG. 6 shows tandem lead apparatuses (RA and RV) in the right heart. In some embodiments, it may be advantageous to deploy RV and RA lead apparatuses each having a reference sensor or a single RV or RA lead apparatus having a multiplicity of spaced-apart sensors. Such a configuration of spatially distributed sensors affords the opportunity to use locating techniques akin to triangulation for accurately determining the location of the LV lead apparatus, discretely or continuously.

For example, multilateration, also known as hyperbolic positioning, may be used to locate the LV lead apparatus 56 by computing the time difference of arrival (TDOA) of a signal emitted from the LV lead apparatus sensor to three or more receiving sensors disposed on one or both of the RV and RA lead apparatuses. A variation of this approach may be used, by which the LV lead apparatus sensor receives a synchronized signal transmitted from three or more spatially separated sensors disposed on one or both of the RV and RA lead apparatuses. In this configuration, the location of the LV lead apparatus sensor may be determined by measuring the TDOA of the synchronized signals transmitted from the spatially separated sensors disposed on one or both of the RV and RA lead apparatuses.

Trilateration is another method that may be used to determine the location of the LV lead apparatus sensor relative to two or more spatially separated sensors disposed on one or both of the RV and RA lead apparatuses. Trilateration uses the relative fixed (i.e., known) locations of two or more right heart reference sensors, and the measured distance between the LV lead apparatus sensor and each reference sensor. Algorithms for implementing a multilateration and trilateration measuring methodology are well known to those skilled in the art.

FIGS. 7 and 8 are tables that may be used to store and/or display information that may be useful to the physician during a lead placement procedure. FIG. 7 provides distance measurement information, while FIG. 8 provides mechanical timing measurement information. Although not shown, a similar table may be used to provide electrical timing or delay measurement information. FIG. 7 tabulates separation distances between the LV lead apparatus 56 relative to various reference or anchor sensors of the RV lead apparatus 54, RA lead apparatus 52, and other reference sensors that may be deployed at each of the discrete LV positions (e.g., positions 1 and 2) shown in FIG. 6.

FIG. 8 shows various mechanical and timing characteristics for each of the discrete LV positions shown in FIG. 6. These characteristics include local maximum strain, time to peak displacement, and other mechanical timing characteristic that may be of interest. As previously discussed, electrical activity and timing data may be similarly tabulated and presented to the physician. These data may be presented in real-time in a manner useful to the physician during lead placement. Moreover, these data (and data derived from these data) may be combined to provide additional useful information, such as electro-mechanical delay data.

FIGS. 9A-10B show strain maps or portions thereof that may be developed in accordance with embodiments of the present invention and presented to the physician to aid in lead placement. The strain maps of FIGS. 9A-10 demonstrate that local strain information may be derived from distance measurements made using distance sensors of the present invention (e.g., ultrasonic microcrystal sensors). FIGS. 9A and 9B show circumferential and longitudinal strain maps, respectively, that may be derived using a distance measuring technique of the present invention. It is noted that the strain estimation methodology is the same for the two maps. The arrangement of the sensors, however, is different. In the case of ultrasonic microcrystal sensors, the sensor crystals are oriented along the length of the heart (from base to apex) to obtain longitudinal strain and along the circumference of the heart to obtain circumferential strain. The lead or sensor arrangement may be placed in either orientation to obtain similar strain maps to identify the strained regions.

FIGS. 10A and 10B are exploded views of longitudinal and circumferential strain map information for RV, septal, and LV regions of the left ventricle. The maps may be used to facilitate a visual understanding of the stress profile of a given region of the heart, such as by highlighting regions of high/maximum stress or uniform stress.

Figure 11:
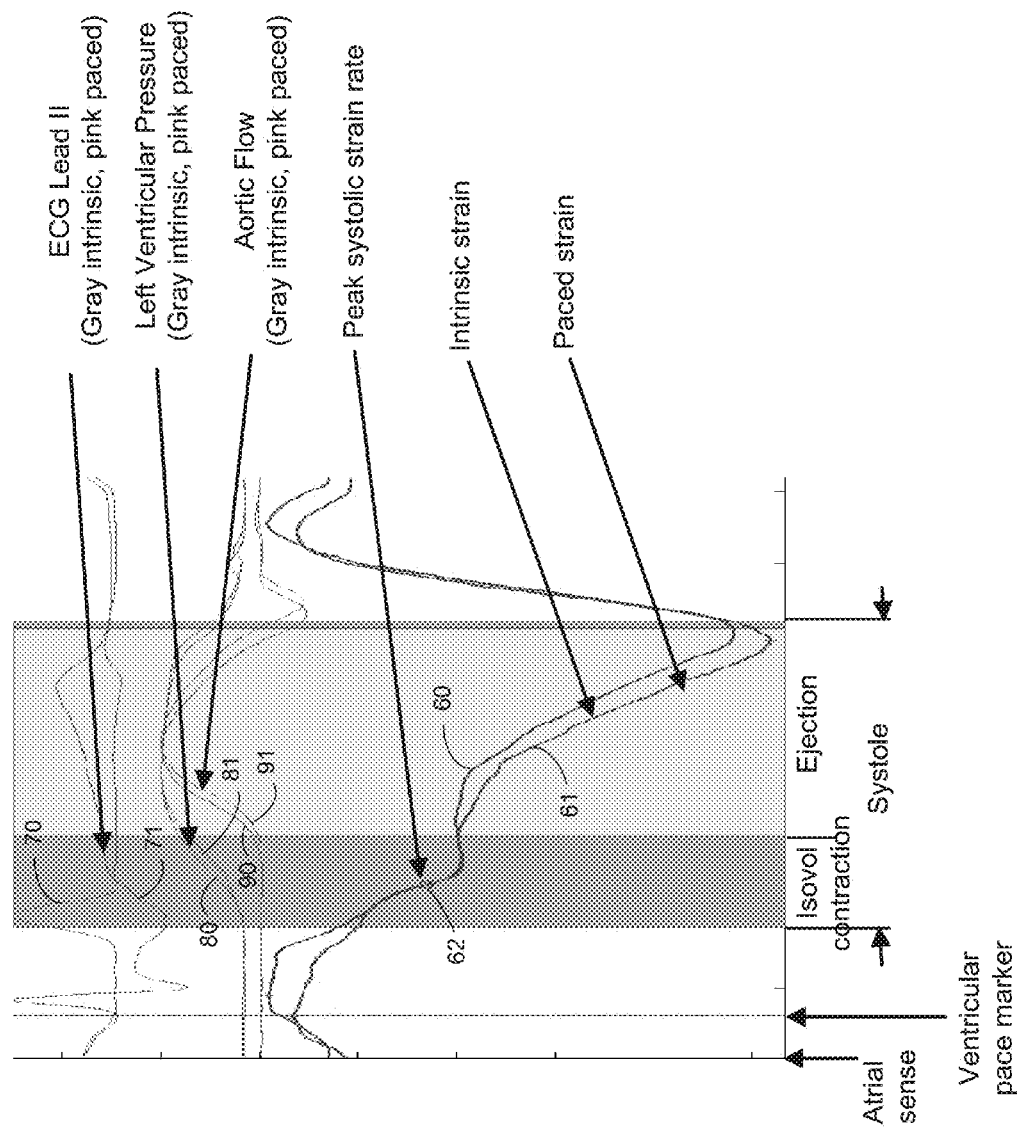
FIG. 11 is a plot of ventricular tissue strain measured during a cardiac cycle using a distance-based measuring technique in accordance with embodiments of the present invention.

FIG. 11 is a plot of ventricular tissue strain measured during a cardiac cycle using a distance-based measuring technique in accordance with the present invention. The strain signal is shown in time-alignment with an ECG signal, a left ventricular pressure signal, and an aortic flow signal. In particular, FIG. 11 shows each of these signals for an intrinsic and a paced beat (intrinsic and paced strain signals 60 and 61; ECG intrinsic and paced signals 70 and 71; intrinsic and paced LV pressure signals 80 and 81; and intrinsic and paced aortic flow signals 90 and 91). The plot of FIG. 11 may be used by the physician to evaluate all portions of the cardiac cycle in terms of strain or stress.

It is theorized that a region of ventricular tissue that experiences greatest strain or strain rate during a cardiac cycle is also the region associated with the largest electrical delay. The strain/ECG profile of FIG. 11 allows the physician to visually evaluate and identify highly stressed regions as candidate pacing sites, such as a location associated with a peak systolic strain rate 62 shown in FIG. 11. Some studies have suggested that the strain rate during isovolumetric contraction is of particular interest, while other studies have suggested that strain rate during the ejection phase is of particular interest. The strain/ECG profile of FIG. 11 allows the physician evaluate stressed regions as candidate pacing sites for each of these phases. For example, the strain curves and the ECG can be used to determine peak strain during a particular period of interest, such as systolic phase, ejection phase, etc., any of which may be used based on physician preference. Electro-mechanical timing information can also be obtained from such a set up.

Figure 12:
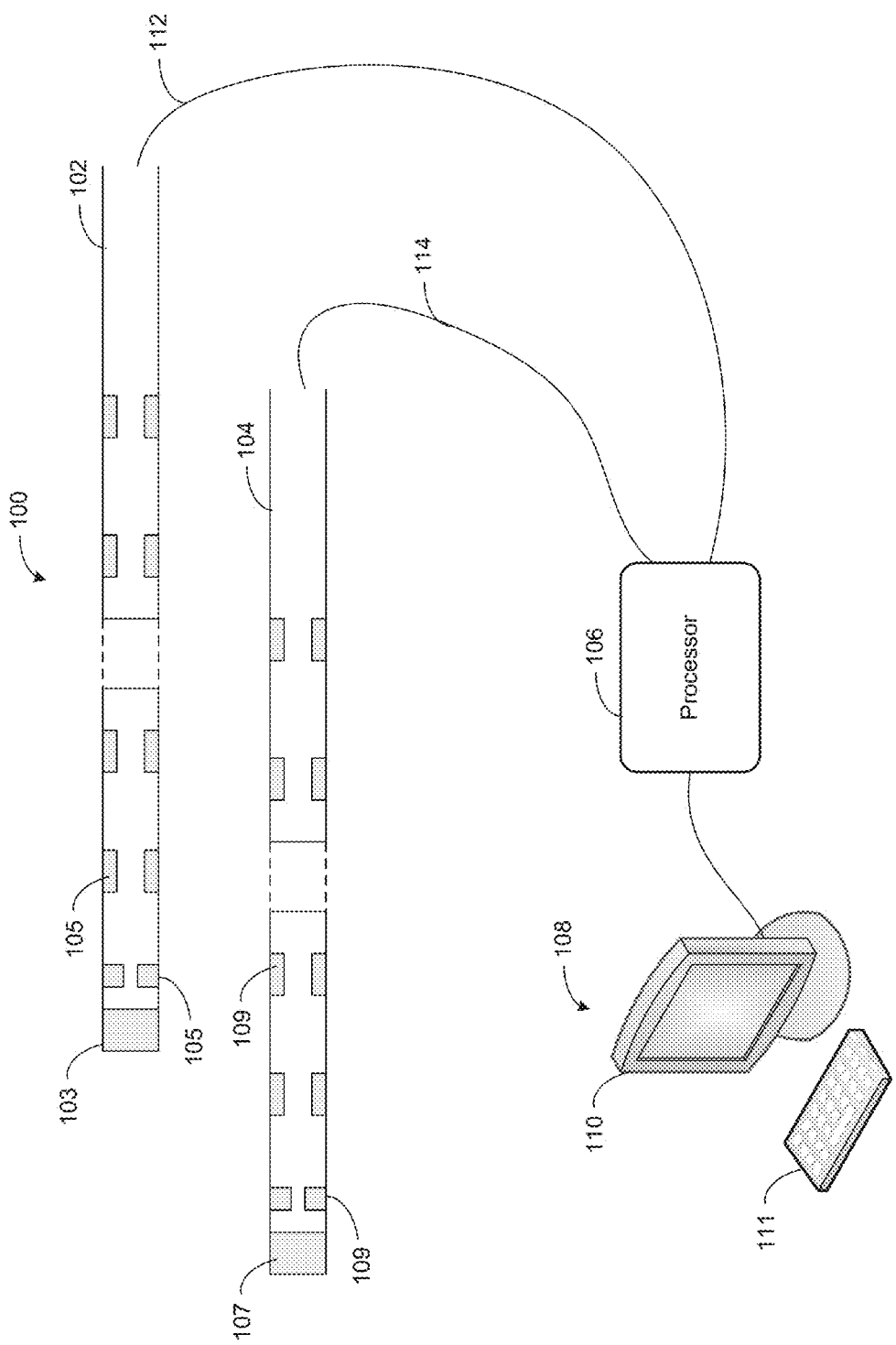
FIG. 12 illustrates a system for facilitating lead placement in accordance with embodiments of the present invention.

FIG. 12 illustrates a system for facilitating lead placement in accordance with embodiments of the present invention. The system 100 shown in FIG. 12 includes a first lead apparatus 102 and a second lead apparatus 104. Each of the lead apparatuses 102, 104 supports one or more sensors 105, 109 configured to facilitate distance measurements in manners discussed hereinabove. Although the lead apparatuses 102, 104 are each shown to support several sensors 105, 109, it is understood that one or both of the lead apparatuses 102, 104 may support only a single sensor 105, 109. As previously discussed, the sensors 105, 109 can be configured as ultrasonic sensors (e.g., ultrasonic microcrystal sensors), piezoelectric sensors, piezoresistive sensors, strain sensors, accelerometers, optical displacement or deformation sensors, among others. For example, the sensors 105, 109 can be ultrasonic sensors including a piezoelectric crystal that operates as an ultrasound transmitter when a drive signal is applied to it or as an ultrasound receiver. When operating as an ultrasound receiver, one of the sensors 105, 109 converts impinging ultrasound energy transmitted from the other of the sensors 105, 109 operating as an ultrasound transmitter into an electrical signal. The time delay between the generation of the transmitted ultrasound signal and the reception of the ultrasound signal varies as a function of a distance between the ultrasound transmitter and the ultrasound receiver. The lead apparatuses 102, 104 may be configured to include one or more electrodes 103, 107.

The lead apparatuses 102, 104 are coupled to a processor 106, typically by electrical or optical conductors 112, 114 that extend from the proximal end of the lead apparatuses 102, 104. The processor 106 is coupled to a user interface 108, which typically includes a display 110 and a user input device 111. The processor 106 is configured to implement the algorithms and methods discussed previously to facilitate lead placement. The system shown in FIG. 12 may be implemented to facilitate lead placement in manners described hereinabove and in accordance with embodiments of the present invention.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

We claim:

1. A system for facilitating placement of a lead in or on a patient's heart, comprising:
   a first lead apparatus including a reference sensor element;
   a second lead apparatus including a cardiac electrode and at least one lead apparatus sensor element;
   a user interface; and
   a processor coupled to the user interface, the reference sensor element, and the lead apparatus sensor element, wherein when the system is in use with the reference sensor element positioned at a right heart location in either a right atrium or a right ventricle, the cardiac electrode positioned at a left heart site of the patient's heart, and the lead apparatus sensor element positioned at one of a plurality of left heart locations in a left ventricle or a coronary venous pathway of the patient's heart, the processor is configured to measure, using signals produced by the reference sensor element and the at least one lead apparatus sensor element, a distance parameter indicative of a distance between the reference sensor element at the right heart location and the at least one lead apparatus sensor element at each of the plurality of left heart locations in either the left ventricle or a coronary venous pathway by computing a time difference of arrival of a signal emitted from the reference sensor element, at the at least one lead apparatus sensor element, determine a separation distance for each of the plurality of left heart locations from the right heart location based on the distance parameter measurements, and determine that the separation distance for a location of the plurality of left heart locations from the right heart location is less than a threshold distance based on the separation distance for the location, the threshold distance representative of unsuitability for pacing, the processor configured to cause the interface to produce a physician perceivable output indicating the unsuitability for pacing at the location.

2. The system of claim 1, wherein the first lead apparatus and second lead apparatus each comprise one or more electrodes configured for electrical stimulation of cardiac tissue.

3. The system of claim 1, wherein the first lead apparatus comprises a catheter, and the second lead apparatus comprises a cardiac electrical lead having one or more electrodes configured for electrical stimulation of cardiac tissue.

4. The system of claim 1, wherein the reference sensor element and the apparatus sensor element respectively comprise an ultrasonic sensor.

5. The system of claim 1, wherein the reference sensor element and the apparatus sensor element respectively comprise a piezoelectric sensor.

6. The system of claim 1, wherein the user interface comprises a display, and the processor is configured to display an alert or warning indicating that the separation distance for the location of the plurality of left heart locations from the right heart location is less than the threshold distance for physician viewing on the display during lead placement.

7. The system of claim 1, further including a third lead apparatus configured for positioning a second reference sensor element at a right heart location, wherein the right heart location is in right atrium if the first lead apparatus is in the right ventricle, or the right heart location is in the right ventricle if the first lead apparatus is in the right atrium, wherein the processor is further coupled to the second reference sensor element, the processor configured to determine a location of the second lead apparatus using signals produced by the reference sensor element, the second reference sensor element, and the at least one lead apparatus sensor element.

8. The system of claim 7, wherein the third lead apparatus further includes a third reference sensor element and the processor is further coupled to the third reference sensor element, wherein the processor is configured determine the location of the second lead apparatus using signals produced by the reference sensor element, the second reference sensor element, the third reference sensor element, and at least one lead apparatus sensor element.

9. The system of claim 8, wherein the processor is configured to determine the location of the at least one lead apparatus sensor element on the second lead apparatus by computing a time difference of arrival of a signal emitted from the at least one lead apparatus sensor element to each of the reference sensor element, the second reference sensor element, and the third reference sensor element.

* * * * *